US006761494B2

(12) United States Patent
Hsu et al.

(10) Patent No.: US 6,761,494 B2
(45) Date of Patent: Jul. 13, 2004

(54) BUTTON APPARATUS WITH A COMPLEX ELASTIC UNIT

(75) Inventors: Chien-Shih Hsu, Taipei (TW); Yai-Kun Tsai, Pin Chen (TW)

(73) Assignee: Darfon Electronics Corp., Taoyuan (TW)

( * ) Notice: Subject to any disclaimer, the term of this patent is extended or adjusted under 35 U.S.C. 154(b) by 0 days.

(21) Appl. No.: 10/342,208

(22) Filed: Jan. 15, 2003

(65) Prior Publication Data

US 2003/0136658 A1 Jul. 24, 2003

(30) Foreign Application Priority Data

Jan. 24, 2002 (TW) ..................................... 91200687 U

(51) Int. Cl.[7] ............................ B41J 5/08; A01H 13/70

(52) U.S. Cl. ....................... 400/495; 400/491; 400/493; 400/490; 200/343; 200/344

(58) Field of Search ................................. 400/495, 491, 400/493, 490; 200/343, 344

(56) References Cited

U.S. PATENT DOCUMENTS

| | | | | | |
|---|---|---|---|---|---|
| 5,842,798 | A | * | 12/1998 | Su | 400/491 |
| 5,899,617 | A | * | 5/1999 | Tsai | 400/490 |
| 6,284,992 | B1 | * | 9/2001 | Richter | 200/344 |
| 6,491,456 | B2 | * | 12/2002 | Shih et al. | 400/373 |
| 6,555,774 | B1 | * | 4/2003 | Nielsen | 200/343 |

* cited by examiner

*Primary Examiner*—Andrew H. Hirshfeld
*Assistant Examiner*—Marvin P. Crenshaw
(74) *Attorney, Agent, or Firm*—Troxell Law Office PLLC

(57) ABSTRACT

A button apparatus with dual elastic elements includes a base, a key top located above the base, an elevation mechanism, and a complex elastic unit. The elevation mechanism is used to execute lifting and lowering operation between the base and the key top. The complex elastic unit, positioned between the base and the key top for providing resilience to the button apparatus, further includes a lower elastic element mounted on the base and an upper elastic element mounted under the key top. When the button apparatus is operated, an S-shaped resilience pattern can be provided by the complex elastic unit to generate a two-step punch feeling back to the user. Thereby, controllability of the button apparatus can be enhanced.

16 Claims, 3 Drawing Sheets

BUTTON APPARATUS WITH A COMPLEX ELASTIC UNIT

FIELD OF THE INVENTION

The present invention relates to an elastic button apparatus and more particularly to a button apparatus that employs a complex elastic unit to generate a two-step punch for enhancing feedback capability and controllability of the button-pressing operation.

BACKGROUND OF THE INVENTION

Scissors mechanisms are widely used in power mechanical structures. For instances, in heavy load applications, they are adopted in cranes or vertical elevators. In light-duty applications, the scissors mechanisms are also adopted in the button key structures of notebook computers or the like. FIG. 1 shows typically a button apparatus 1 adopted in notebook computers. The button apparatus 1 includes a base 10, a key top 11, an elevation mechanism 12 consisting of a dual-scissors mechanism for connecting the base 10 and the key top 11, and a rubber 13 located in the elevation mechanism 12 (between the two scissors mechanism). The rubber 13 is used to provide resilience for the button-pressing operation.

In conventional techniques, the button apparatus mentioned above usually have an elastic element (such as the rubber 13) to store potential energy and function as a returning mechanism. Such a type of element generally has a fixed elasticity coefficient. Hence, within the application range of the elastic element, a definite elastic relationship between the resilience and the deformation can be provided (as shown by the pattern I in FIG. 2). However, such a simple relationship between the deformation and the resilience sometimes cannot meet the requirements of actual applications. Hence, in some conventional techniques, in order to support larger loads or change the single resilience pattern, it is a common practice to couple elastic elements of different elasticity in parallel to form a relationship between the deformation and the resilience as the one shown by Pattern II in FIG. 2.

Analysis of the relationship between the deformation and the resilience shown by the pattern II in FIG. 2 indicates that a greater deformation can generate a greater loading support or a greater resilience. Though such an application is usually adopted for heavy-duty apparatus such as cranes, yet it hasn't been found in light-duty apparatus such as the button apparatus of notebook computers.

As mentioned above, in the light-duty apparatus, the elastic mechanism of the Pattern II has not been adopted. However, in terms of control and manufacturing, the two-step resilience can provide substantial advantages for those light-duty apparatus, especially for the button apparatus of notebook computers. As the button apparatus is by nature to receive the pressing or hitting impact of users. The construction employing the pattern of two-step resilience enables users to get a better punch feeling (i.e. feedback sense). It helps users to get better control during striking operations. Moreover, from the standpoint of the users of the keyboard, they usually place their fingers on the button keys in advance. The construction employing the pattern of two-step resilience enables users to avoid the risk of "fault-striking".

Nevertheless, to make the button apparatus according to the Pattern II shown in FIG. 2 has two drawbacks. Firstly, the controllability of pressing is not desirable. Secondly, user's fatigue resulting from hitting the button keys tends to accumulate in an accelerating manner. The poor controllability is caused by a greater force required to apply to the button key for generating a preset deformation (as shown by Pattern II in FIG. 2, in which the resilience increases as the deformation increases). Hence, the control feedback sense of pressing operations by steps is not adequate. The acceleration of user's fatigue is caused by the greater force required in the operations (comparing Pattern I with Pattern II in FIG. 2) to reach the preset deformation. As pressing operations take place frequently (for instance, for a user to enter 60 Chinese characters per minute, with one Chinese character requiring average four strikes on the button keys, the user has to strike the keyboard 240 times a minute, or 14400 times an hour). Hence, even a small increase of operation force does affect user's operation continuity, or even result in impact occupational injury.

Therefore, to provide an improved two-step elastic mechanism for small loading button, apparatus such as notebook computers is an important target deserved pursuing.

SUMMARY OF THE INVENTION

The primary object of the invention is to provide an elastic button apparatus that employs a complex elastic unit for enabling users to operate with two-step resilience so as to enhance feedback sense and controllability.

The elastic button apparatus of the invention includes a base, a key top, an elevation mechanism and a complex elastic unit. The key top is located above the base. The elevation mechanism is located between the base and the key top for guiding lifting and lowering operations of the key top. The complex elastic unit is located also between the key top and the base to provide resilience to the button apparatus to perform lifting and lowering operations. The complex elastic unit includes a lower elastic element located on the base and an upper elastic element located below the key top. While the elastic button apparatus is lifting or lowering, the complex elastic unit generates an S-shaped resilience pattern through the compression of the upper elastic element and the lower elastic element, in response to the decrease of the spacing between the key top and the base.

In the invention, the elevation mechanism employed in the elastic button apparatus may be a scissors mechanism.

In one embodiment of the invention, the lower elastic element may be a conical rubber with the convex side pointing upwards or a conical metal cape with the convex side pointing upwards.

In one embodiment according to the one set forth above, the upper elastic element corresponding to the lower elastic element may be a pair of repulsive magnets located on a bottom side of the key top and a top end of the lower elastic element, respectively.

In one embodiment according to the one set forth above, the upper elastic element corresponding to the lower elastic element may be a pair of repulsive magnets located on a bottom side of the key top and a bottom end of the lower elastic element, respectively.

In another embodiment according to the one set forth above, the upper elastic element may be a conical rubber with the convex side facing downwards, a conical metal cape with the convex side facing downwards, a compression spring or an elastic element of the like.

In another embodiment of the invention, the upper elastic element may be a conical rubber with the convex side facing downwards or a conical metal cape with the convex side facing downwards.

In one embodiment according to the one set forth above, the lower elastic element corresponding to the upper elastic element may be a pair of repulsive magnets located on the base and a bottom end of the upper elastic element, respectively.

In one embodiment according to the one set forth above, the lower elastic element corresponding to the upper elastic element may be a pair of repulsive magnetic elements located on the base and a top end of a bottom section of the upper elastic element, respectively.

In another embodiment according to the one set forth above, the lower elastic element may be a conical rubber with the convex side facing upwards, a conical metal cape with the convex side facing upwards, a compression spring or an elastic element of the like.

The elastic button apparatus of the invention may be adapted on keyboards or devices with like button structures. For instances, when the elastic button apparatus is directly used on a keyboard, the keyboard includes a base and a plurality of elastic button apparatus located on the base.

The foregoing, as well as additional objects, features and advantages of the invention will be more readily apparent from the following detailed description, which proceeds with reference to the accompanying drawings.

DESCRIPTION OF THE PREFERRED EMBODIMENTS

In the following description, elements of same function will be marked by same name and numerals even if they are formed in different shapes to maintain the consistency of explanation of the invention.

In the invention, the definition of "quasi-rigid elastic element" is an elastic element with the properties that: a significant elastic deformation can incur after a force exceeding a preset pressure is applied. In conventional techniques, conical metal capes or conical rubbers are such types of elastic element.

In the invention, the definition of "non-rigid elastic element" is an elastic element with the properties that: a corresponding elastic deformation can incur at the beginning of a force being applied. In general, springs, repulsive magnets, or conical metal capes or conical rubbers with a very small thickness are such types of elastic element.

Figure 1:
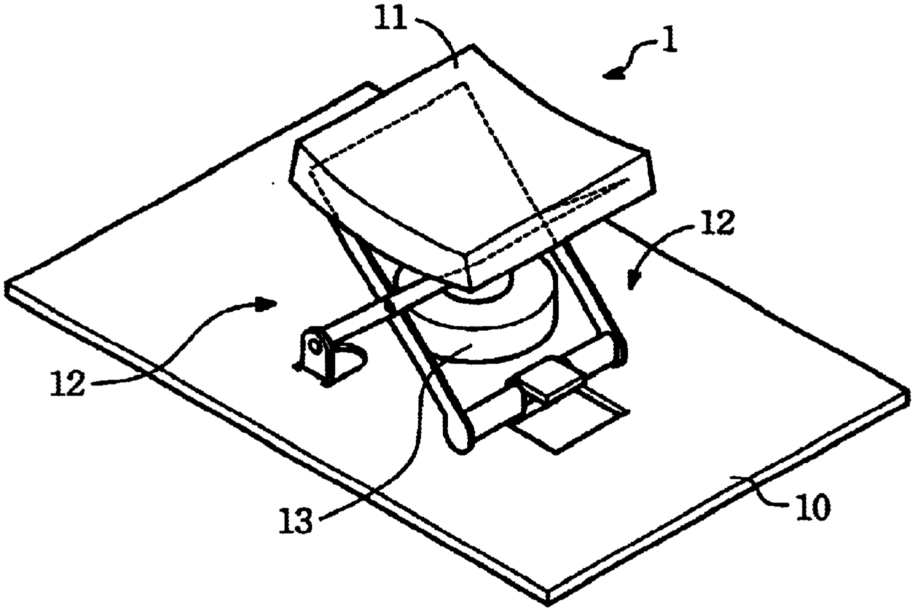
FIG.1 (PRIOR ART)
FIG. 1 is a perspective view of a button key structure for a notebook computer.
Figure 3A:
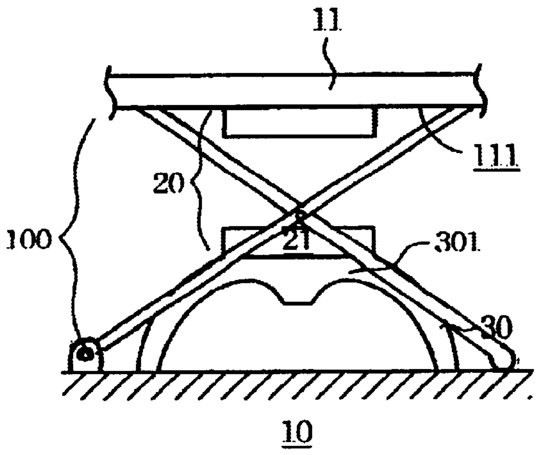
FIG. 3A is a schematic side view of a first embodiment of the elastic button apparatus of the invention.

Refer to FIG. 3A for a first embodiment of the elastic button apparatus of the invention. The elastic button apparatus includes a base 10, a key top 11, an elevation mechanism (not shown in the drawing to make the drawing clean, but referring to FIG. 1 for its relative position), and a complex elastic unit 100. Similar to the conventional construction set forth above, the key top 11 is located above the base 10. The elevation mechanism (not shown in the drawing) is located between the base 10 and the key top 11 for guiding lifting and lowering operations of the key top 11 above the base 10. The complex elastic unit 100 is also located between the key top 11 and the base 10 for providing resilience to the button apparatus for lifting and lowering operations.

In the invention, the complex elastic unit 100 may include a lower elastic element 30 located on the base 10 and an upper elastic element 20 located below the key top 11. Either the lower elastic element 30 or the upper elastic element 20 is a quasi-rigid elastic element, while the other is a non-rigid elastic element. As shown in FIG. 3A, the upper elastic element 20 is a pair of repulsive magnets (i.e. with the same N or S poles facing each other). The lower elastic element 30 is a conical metal cape or a conical rubber.

Figure 3B:
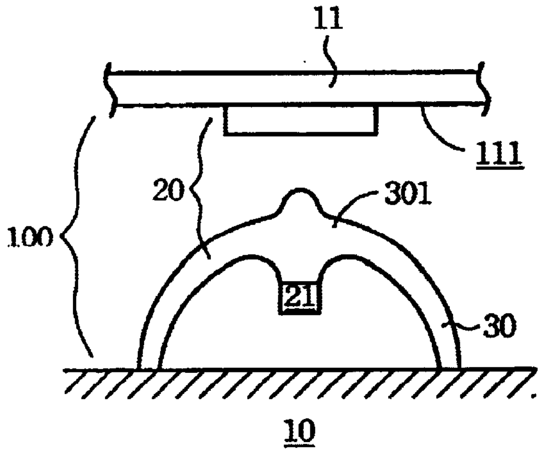
FIG. 3B is a schematic side view of an embodiment variation of the first embodiment of the invention according to FIG. 3A.

Refer to FIGS. 3A and 3B for a same embodiment but with slightly different positioning of the elements. As shown in FIG. 3A, a lower magnet 21 of the upper elastic element 20 is located on a top end 301 of the lower elastic element 30. Referring to FIG. 3B, the lower magnet 21 of the upper elastic element 20 is located on the bottom side of the top end 301 of the lower elastic element 30. It is obvious that both structures set forth above do not affect the operation of the upper elastic element 20.

Figure 4:
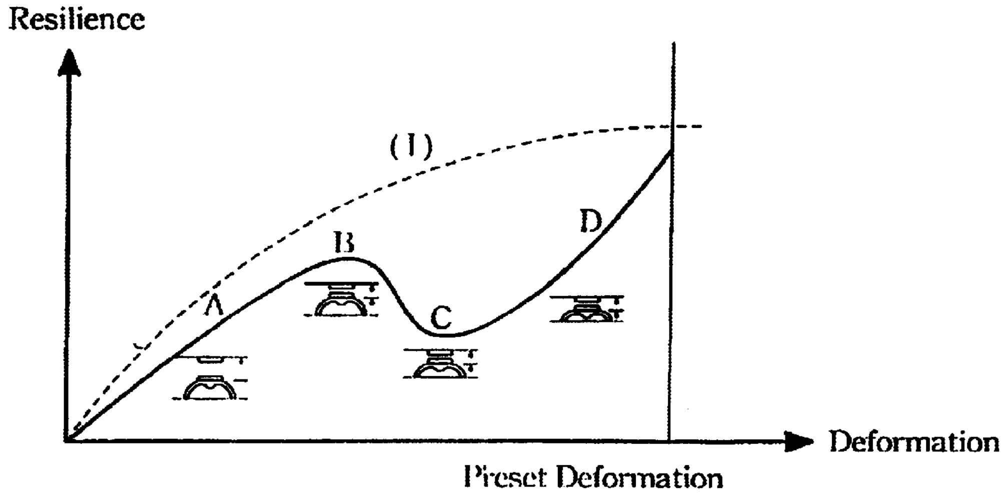
FIG. 4 is a chart showing the relationship between the deformation and resilience for the embodiment shown in FIG. 3.

Referring to FIG. 4, in the case that the elastic button apparatus of the invention is subjected to a force (shown by the A section in the drawing) and the force does not reach the preset pressure of the lower elastic element 30 (quasi-rigid elastic element), the lower elastic element 30 will behave like a rigid element without deforming while a deformation does occur on the upper elastic element 20 (non-rigid elastic element) by the force.

At the point that the force reaches the point B, the force is understood to just hit the preset pressure of the lower elastic element 30. Hence, after passing the B point, the two elastic elements of the complex elastic unit 100 connect in series. It is obvious that the elasticity coefficient of the combined structure is smaller than the individual elasticity coefficient of the lower elastic element 30 or the upper elastic element 20. Hence, at that moment, the resilience drops sharply and deformation increases.

When the deformation reaches C point, the jump of the complex elastic unit 100 can reach a stable point. Thus, the complex elastic unit 100 generates deformation contributed by both elastic elements.

Figure 2:
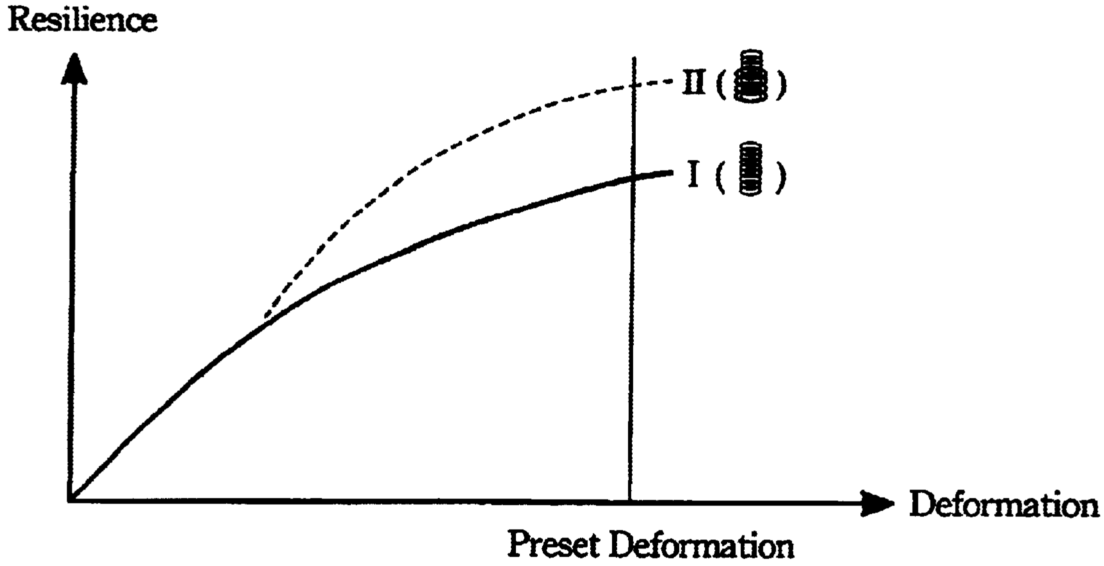
FIG.2 (PRIOR ART)
FIG. 2 is a chart showing the relationship between the deformation and resilience of two types of conventional elastic assembly.

In the section D of the FIG. 2, the complex elastic unit 100 generates deformation contributed by both elastic elements. However, due to increasing of deformation, either the upper elastic element 20 or the lower elastic element 30 gradually reaches respective dead points of the deformation. Hence, total elasticity coefficient gradually increases. Therefore, in the section D of FIG. 4, the gradient (resilience/deformation) is not a constant.

As shown in FIG. 4, when the elastic button apparatus is in lifting or lowering operation, the complex elastic unit 100, due to shrinking spacing between the key top 11 and the base 10 (so as the continual compression of the upper elastic element 20 and the lower elastic element 30), generates an S-shaped resilience (or resistance) pattern. Such a phenomenon enables users to clearly feel the jump of the complex elastic unit 100. Hence, the feedback sense of the entire apparatus becomes remarkable. As described above, with the two elastic elements coupled in series, the combined elasticity coefficient is smaller than the elasticity coefficient of each individual elastic element. Thus, the force required by users to strike the button key can be reduced.

In the invention, the elevation mechanism 12 being adopted may be a scissors mechanism. The complex elastic unit 100 can be located on one side of the scissors mechanism, or in the middle portion of the dual-scissors mechanism.

Figure 5:
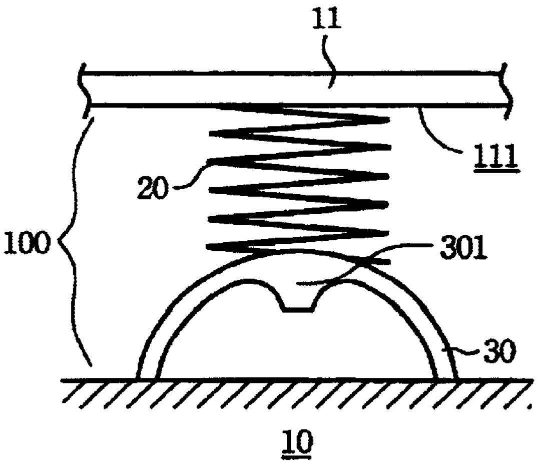
FIG. 5 is a schematic side view of a second embodiment of the elastic button apparatus of the invention.
Figure 6:
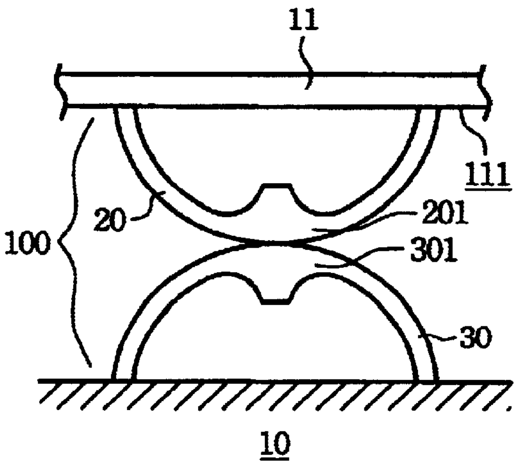
FIG. 6 is a schematic side view of a third embodiment of the elastic button apparatus of the invention.
Figure 7:
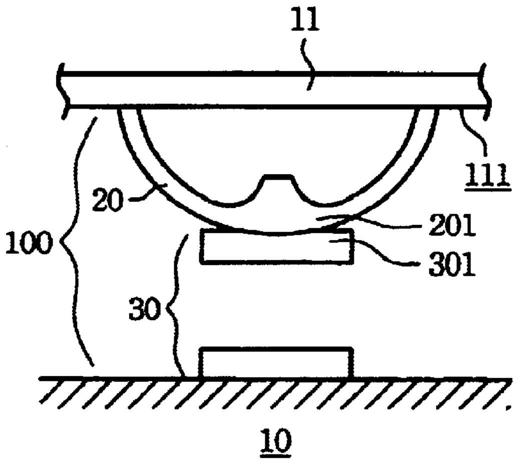
FIG. 7 is a schematic side view of a fourth embodiment of the elastic button apparatus of the invention.
Figure 8:
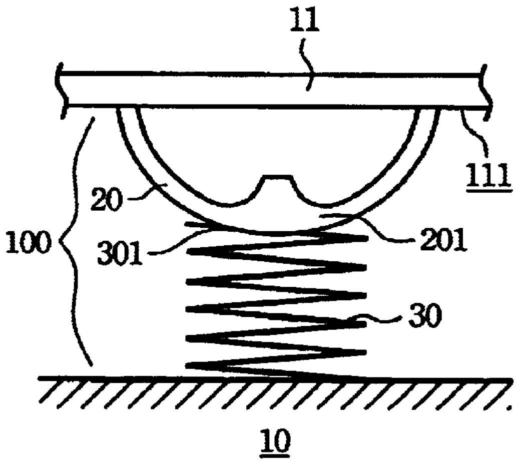
FIG. 8 is a schematic side view of a fifth embodiment of the elastic button apparatus of the invention.

As mentioned above, the upper elastic element 20 and the lower elastic element 30 of the complex elastic unit 100 may be respectively a quasi-rigid elastic element and a non-rigid elastic element, or a non-rigid elastic element and a quasi-rigid elastic element. Referring to FIG. 5, the upper elastic element 20 and the lower elastic element 30 are respectively a compression spring (a non-rigid elastic element) and a conical rubber with the convex side facing upwards (or a conical metal cape with the convex side facing upwards) (as a quasi-rigid elastic element). Referring to FIG. 6, the upper elastic element 20 and the lower elastic element 30 are respectively a thin wall conical rubber with the convex side facing downwards (or a conical metal cape with the convex side facing downwards) (as a non-rigid elastic element) and a thick wall conical rubber with the convex side facing upwards (or a conical metal cape with the convex side facing upwards) (as a quasi-rigid elastic element). Referring to FIG. 7, the pairing of the upper elastic element 20 and the lower elastic element 30 is formed by a conical rubber with the convex side facing downwards (or a conical metal cape with the convex side facing downwards) (as a quasi-rigid elastic element) and a pair of repulsive magnets (both as non-rigid elastic elements). Referring to FIG. 8, the upper elastic element 20 and the lower elastic element 30 are respectively a conical rubber with the convex side facing downwards (or a conical metal cape with the convex side facing downwards) (as a quasi-rigid elastic element) and a compression spring (as a non-rigid elastic element).

In the embodiments set forth above, the elastic button apparatus is being adopted in a button key or a keyboard. The keyboard includes a base and a plurality of elastic button apparatus located on the base according to a preset configuration. Of course, the elastic button apparatus of the invention may also be adopted on other similar apparatus such as elevation apparatus.

In the invention, by means of arrangements of materials and elements, the complex elastic unit may obtain an S-shaped resilience pattern as shown in FIG. 4. As to how to achieve an optimal design, there are still various factors to be considered, such as implementation conditions, design loading, stroke distance, etc. Nevertheless, these considerations are known to people skilled in the art. Thus, details are omitted herein.

By means of the invention, and through employing the complex elastic unit which consists of a quasi-rigid elastic element and a non-rigid elastic element, users may get two-step pressing resilience in an S-shaped resilience pattern as shown in FIG. 4. As a result, feed back sense and controllability for pressing operations can thus be enhanced effectively.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. An elastic button apparatus with an elevation mechanism, the elastic button apparatus comprising:

a base;

a key top, located above the base, the elevation mechanism located between the base and the key top and guiding lifting and lowering operation of the key top above the base; and a complex elastic unit, located between the key top and the base for providing resilience to the lifting and lowering operations including a lower elastic element located on the base and an upper elastic element located below the key top;

wherein the complex elastic unit generates an S-shaped resilience pattern during the lifting and lowering operations through decreasing of spacing between the key top and the base and compression of the upper elastic element and the lower elastic element, wherein the lower elastic element is a conical elastic element with a convex side facing upwards, and wherein the upper elastic element is a pair of repulsive magnets located respectively on a bottom side of the key top and a top end of the lower elastic element.

2. An elastic button apparatus with an elevation mechanism, the elastic button apparatus comprising:

a base;

a key top, located above the base, the elevation mechanism located between the base and the key top and guiding lifting and lowering operation of the key top above the base; and a complex elastic unit, located between the key top and the base for providing resilience to the lifting and lowering operations including a lower elastic element located on the base and an upper elastic element located below the key top;

wherein the complex elastic unit generates an S-shaped resilience pattern during the lifting and lowering operations through decreasing of spacing between the key top and the base and compression of the upper elastic element and the lower elastic element, wherein the lower elastic element is a conical elastic element with a convex side facing upwards, and wherein the upper elastic element is a pair of repulsive magnets located respectively on a bottom side of the key top and a bottom end of a top section of the lower elastic element.

3. An elastic button apparatus with an elevation mechanism, the elastic button apparatus comprising:

a base;

a key top, located above the base, the elevation mechanism located between the base and the key top and guiding lifting and lowering operation of the key top above the base; and a complex elastic unit, located between the key top and the base for providing resilience to the lifting and lowering operations including a lower elastic element located on the base and an upper elastic element located below the key top;

wherein the complex elastic unit generates an S-shaped resilience pattern during the lifting and lowering operations through decreasing of spacing between the key top and the base and compression of the upper elastic element and the lower elastic element, wherein the lower elastic element is a conical elastic element with a convex side facing upwards, and wherein the upper elastic element is a compression spring.

4. An elastic button apparatus with an elevation mechanism, the elastic button apparatus comprising:

a base;

a key top, located above the base, the elevation mechanism located between the base and the key top and guiding lifting and lowering operation of the key top above the base; and a complex elastic unit, located between the key top and the base for providing resilience to the lifting and lowering operations including a lower elastic element located on the base and an upper elastic element located below the key top;

wherein the complex elastic unit generates an S-shaped resilience pattern during the lifting and lowering operations through decreasing of spacing between the key top and the base and compression of the upper elastic element and the lower elastic element, wherein the lower elastic element is a conical elastic element with a convex side facing upwards, and wherein the upper elastic element is a conical metal cape with a convex side facing downwards.

5. An elastic button apparatus with an elevation mechanism, the elastic button apparatus comprising:

a key top, located above the base, the elevation mechanism located between the base and the key top and guiding lifting and lowering operation of the key top above the base; and a complex elastic unit, located between the key top and the base for providing resilience to the lifting and lowering operations including a lower elastic element located on the base and an upper elastic element located below the key top;

wherein the complex elastic unit generates an S-shaped resilience pattern during the lifting and lowering operations through decreasing of spacing between the key top and the base and compression of the upper elastic element and the lower elastic element, wherein the upper elastic element is a conical elastic element with a convex side facing downwards; and wherein the lower elastic element is a pair of repulsive magnets located respectively on the base and a bottom end of the upper elastic element.

6. An elastic button apparatus with an elevation mechanism, the elastic button apparatus comprising:

a base;

a key top, located above the base, the elevation mechanism located between the base and the key top and guiding lifting and lowering operation of the key top above the base; and a complex elastic unit, located between the key top and the base for providing resilience to the lifting and lowering operations including a lower elastic element located on the base and an upper elastic element located below the key top;

wherein the complex elastic unit generates an S-shaped resilience pattern during the lifting and lowering operations through decreasing of spacing between the key top and the base and compression of the upper elastic element and the lower elastic element, wherein the upper elastic element is a conical elastic element with a convex side facing downwards; and wherein the lower elastic element is a pair of repulsive magnets located respectively on the base and a top end of a bottom section of the upper elastic element.

7. An elastic button apparatus with an elevation mechanism, the elastic button apparatus comprising:

a base;

a key top, located above the base, the elevation mechanism located between the base and the key top and guiding lifting and lowering operation of the key top above the base; and a complex elastic unit, located between the key top and the base for providing resilience to the lifting and lowering operations including a lower elastic element located on the base and an upper elastic element located below the key top;

wherein the complex elastic unit generates an S-shaped resilience pattern during the lifting and lowering operations through decreasing of spacing between the key top and the base and compression of the upper elastic element and the lower elastic element, wherein the upper elastic element is a conical elastic element with a convex side facing downwards; and wherein the lower elastic element is a compression spring.

8. An elastic button apparatus with an elevation mechanism, the elastic button apparatus comprising:

a base;

a key top, located above the base, the elevation mechanism located between the base and the key top and guiding lifting and lowering operation of the key top above the base; and a complex elastic unit, located between the key top and the base for providing resilience to the lifting and lowering operations including a lower elastic element located on the base and an upper elastic element located below the key top;

wherein the complex elastic unit generates an S-shaped resilience pattern during the lifting and lowering operations through decreasing of spacing between the key top and the base and compression of the upper elastic element and the lower elastic element, wherein the upper elastic element is a conical elastic element with a convex side facing downwards; and wherein the lower elastic element is a conical metal cape with a convex side facing upwards.

9. A keyboard with at least one elevation mechanism, the keyboard comprising:

a base; and a plurality of button apparatus, located on the base according to a preset configuration, wherein at least one of the plurality of button apparatus includes:

a key top, the elevation mechanism located between the base and the key top and guiding pressing operation of the button apparatus located above the base; and a complex elastic unit, located between the key top and the base for providing resilience to the pressing operations including a lower elastic element located on the base and an upper elastic element located below the key top;

wherein the complex elastic unit generates an S-shaped resilience pattern during the pressing operations of the button apparatus through decreasing of the upper elastic element and the lower elastic element, wherein the upper elastic element is a conical elastic element with a convex side facing downwards, and wherein the lower elastic element is a pair of repulsive magnets located respectively on the base and a bottom end of the upper elastic element.

10. A keyboard with at least one elevation mechanism, the keyboard comprising:

a base; and a plurality of button apparatus, located on the base according to a preset configuration, wherein at least one button apparatus includes:

a key top, the elevation mechanism located between the base and the key top and guiding pressing operation of the button apparatus located above the base; and a complex elastic unit, located between the key top and the base for providing resilience to the pressing operations including a lower elastic element located on the base and an upper elastic element located below the key top;

wherein the complex elastic unit generates an S-shaped resilience pattern during the pressing operations of the button apparatus through decreasing of the upper elastic element and the lower elastic element, wherein the upper elastic element is a conical elastic element with a convex side facing downwards, and wherein the lower elastic element is a pair of repulsive magnets located respectively on the base and a top end of a bottom section of the upper elastic element.

11. A keyboard with at least one elevation mechanism, the keyboard comprising:

a base; and a plurality of button apparatus, located on the base according to a preset configuration, wherein at least one button apparatus includes:

a key top, the elevation mechanism located between the base and the key top and guiding pressing operation of the button apparatus located above the base; and a complex elastic unit, located between the key top and the base for providing resilience to the pressing operations including a lower elastic element located on the base and an upper elastic element located below the key top;

wherein the complex elastic unit generates an S-shaped resilience pattern during the pressing operations of the button apparatus through decreasing of the upper elastic element and the lower elastic element, wherein the upper elastic element is a conical elastic element with a convex side facing downwards, and wherein the lower elastic element is a compression spring.

12. A keyboard with at least one elevation mechanism, the keyboard comprising:

a base; and a plurality of button apparatus, located on the base according to a preset configuration, wherein at least one button apparatus includes:

a key top, the elevation mechanism located between the base and the key top and guiding pressing operation of the button apparatus located above the base; and a complex elastic unit, located between the key top and the base for providing resilience to the pressing operations including a lower elastic element located on the base and an upper elastic element located below the key top;

wherein the complex elastic unit generates an S-shaped resilience pattern during the pressing operations of the button apparatus through decreasing of the upper elastic element and the lower elastic element, wherein the upper elastic element is a conical elastic element with a convex side facing downwards, and wherein the lower elastic element is a conical metal cape with a convex side facing upwards.

13. A keyboard with at least one elevation mechanism, the keyboard comprising:

a base; and a plurality of button apparatus, located on the base according to a preset configuration, wherein at least one button apparatus includes:

a key top, the elevation mechanism located between the base and the key top and guiding pressing operation of the button apparatus located above the base; and a complex elastic unit, located between the key top and the base for providing resilience to the pressing operations including a lower elastic element located on the base and an upper elastic element located below the key top;

wherein the complex elastic unit generates an S-shaped resilience pattern during the pressing operations of the button apparatus through decreasing of the upper elastic element and the lower elastic element, wherein the lower elastic element is a conical elastic element with a convex side facing upwards, and wherein the upper elastic element is a pair of repulsive magnets located respectively on the base and a top end of the lower elastic element.

14. A keyboard with at least one elevation mechanism, the keyboard comprising:

a base; and a plurality of button apparatus, located on the base according to a preset configuration, wherein at least one button apparatus includes:

a key top, the elevation mechanism located between the base and the key top and guiding pressing operation of the button apparatus located above the base; and a complex elastic unit, located between the key top and the base for providing resilience to the pressing operations including a lower elastic element located on the base and an upper elastic element located below the key top;

wherein the complex elastic unit generates an S-shaped resilience pattern during the pressing operations of the button apparatus through decreasing of the upper elastic element and the lower elastic element, wherein the lower elastic element is a conical elastic element with a convex side facing upwards, and wherein the upper elastic element is a pair of repulsive magnets located respectively on a bottom side of the key top and a bottom end of a top section of the lower elastic element.

15. A keyboard with at least one elevation mechanism, the keyboard comprising:

a base; and a plurality of button apparatus, located on the base according to a preset configuration, wherein at least one button apparatus includes:

a key top, the elevation mechanism located between the base and the key top and guiding pressing operation of the button apparatus located above the base; and a complex elastic unit, located between the key top and the base for providing resilience to the pressing operations including a lower elastic element located on the base and an upper elastic element located below the key top;

wherein the complex elastic unit generates an S-shaped resilience pattern during the pressing operations of the button apparatus through decreasing of the upper elastic element and the lower elastic element, wherein the lower elastic element is a conical elastic element with a convex side facing upwards, and wherein the upper elastic element is a compression spring.

16. A keyboard with at least one elevation mechanism, the keyboard comprising:

a base; and a plurality of button apparatus, located on the base according to a preset configuration, wherein at least one button apparatus includes:

a key top, the elevation mechanism located between the base and the key top and guiding pressing operation of the button apparatus located above the base; and a complex elastic unit, located between the key top and the base for providing resilience to the pressing operations including a lower elastic element located on the base and an upper elastic element located below the key top;

wherein the complex elastic unit generates an S-shaped resilience pattern during the pressing operations of the button apparatus through decreasing of the upper elastic element and the lower elastic element, wherein the lower elastic element is a conical elastic element with a convex side facing upwards, and wherein the upper elastic element is a conical metal cape with a convex side facing downwards.

* * * * *